United States Patent [19]

Wilson

[11] Patent Number: 4,987,904
[45] Date of Patent: Jan. 29, 1991

[54] METHOD AND APPARATUS FOR BONE SIZE GAUGING

[76] Inventor: James T. Wilson, 1932 Tampa East Blvd., Tampa, Fla. 33619

[21] Appl. No.: 497,492

[22] Filed: Mar. 22, 1990

[51] Int. Cl.⁵ .............................................. A61B 5/107
[52] U.S. Cl. ........................................ 128/774; 73/762; 73/104; 33/512; 606/53; 606/86; 606/102
[58] Field of Search ............ 33/511, 512, 513, 501.45; 73/104, 762; 128/774, 630; 606/53, 86, 102

[56] References Cited

U.S. PATENT DOCUMENTS

| | | | |
|---|---|---|---|
| 4,135,517 | 1/1979 | Reale | 606/86 |
| 4,509,527 | 4/1985 | Fraden | 128/774 |
| 4,517,969 | 5/1985 | Halcomb, III et al. | 606/102 |
| 4,632,111 | 12/1986 | Roche | 606/53 |
| 4,658,808 | 4/1987 | Link | 33/511 |

Primary Examiner—Ruth S. Smith
Assistant Examiner—Krista M. Pfaffle
Attorney, Agent, or Firm—Dominik, Stein, Saccocio, Reese, Colitz & Van Der Wall

[57] ABSTRACT

A device for gauging the size of a bone socket comprising a hemispherical member having a pole on its axis at the distal end and having a bore on its axis at its proximal end; a handle releasably attached to the bore of the hemispherical member; and a pressure responsive surface on the hemispherical member to constitute a pressure responsive surface for changing characteristics when brought in contact with a bone socket to be gauged. The change in characteristics may be in color or shape. Also disclosed is the method for using the device.

11 Claims, 1 Drawing Sheet

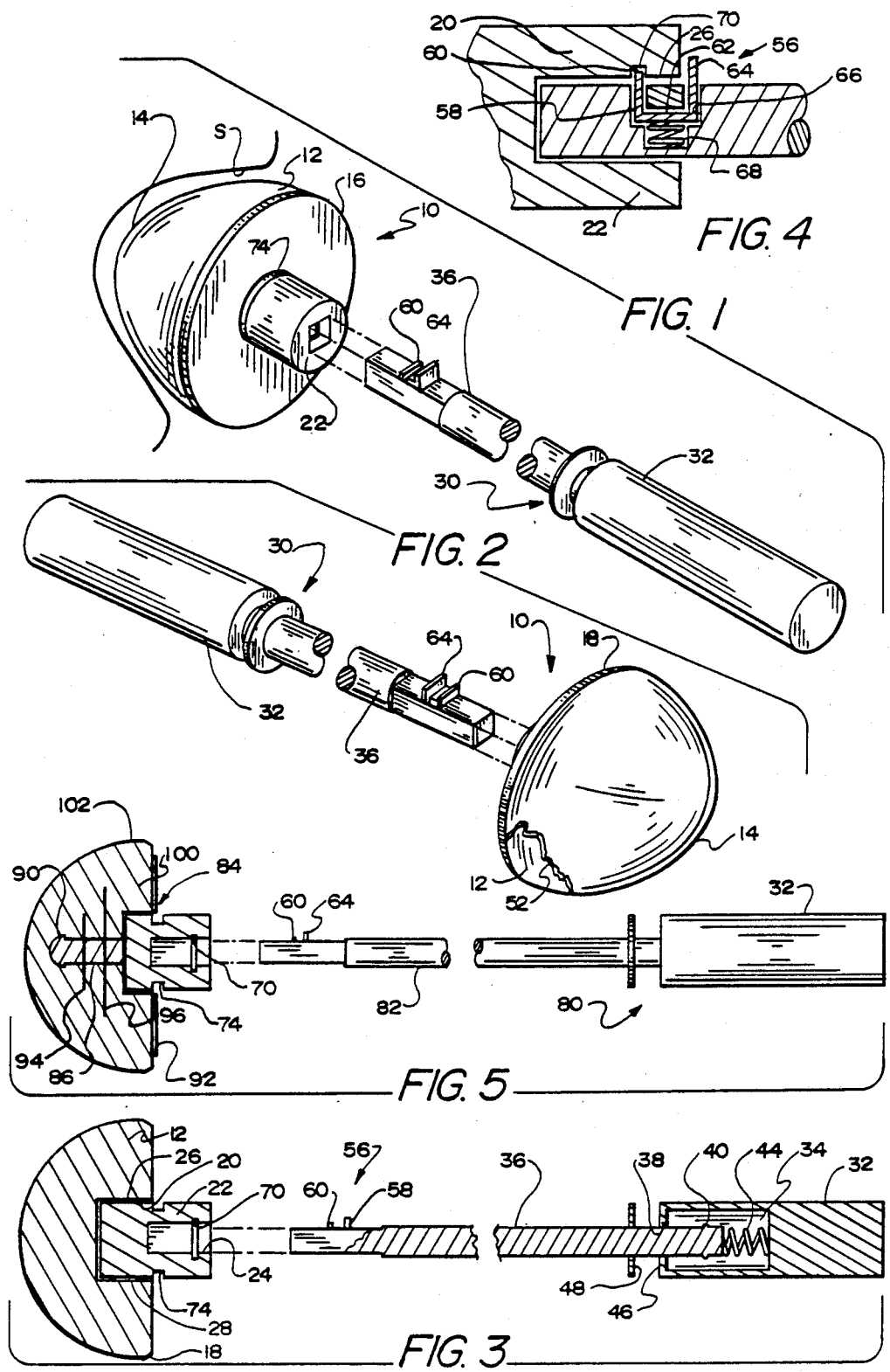

METHOD AND APPARATUS FOR BONE SIZE GAUGING

BACKGROUND OF THE INVENTION

1. Field of the Invention

This invention relates to a method and apparatus for bone size gauging and, more particularly, to the utilization of a hemispherical member with a pressure responsive exterior surface capable of changing characteristics, color or shape, when contacted by a surface into which it is inserted.

2. Description of the Background Art

It is common for orthopedic surgeons to use a testing device or gauge for determining the proper size of prosthetic implant for a socket joint when replacing a patient's natural ball joint. The most common technique involves the surgeon making an initial estimate of the artifical ball to be utilized based upon the patient's x-rays when viewed with overlays and templates. The surgeon will then have available a plurality of test balls of different sizes which might fit properly. During the operation, after the bone-receiving socket has been cleaned, the surgeon will then insert one test ball into the socket and effect a limited degree of rotation or testing movement to feel the fit. Thereafter, the surgeon will then try another ball of a slightly different size. Based on the feel that the surgeon receives from such insertions and testing movements, he would use his judgement and experience to determine the proper ball size to be utilized for the particular socket.

During such procedures, it is only the experience of the surgeon, who has performed such tests before, that can be relied upon for the selection of the proper size ball for a successful implant operation. As such, the practice is limited to use by experienced surgeons and requires extended time to insert, move and determine the proper ball size from a plurality of closely sized balls.

The shortcomings of known methods and apparatus for use by surgeons in determining the proper ball size are evidenced by the large number of patents issued on devices attempting to overcome the deficiencies in the prior art. By way of example, note U.S. Pat. Nos. 2,737,724 to Herz; 4,135,517 to Reale; 4,436,684 to Light; 4,559,936 to Hill: 4,632,111 to Roche; and 4,645,503 to Lin. Each of these patents relates to a method or apparatus for orthopedic bone replacement or the like wherein sizing is a consideration. Note in particular, U.S. Pat. No. 4,517,969 to Halcomb. According to that disclosure, a translucent hemispherical gauge is inserted in a bone socket to be sized. The translucence of the exterior surface, when contacting an area of the bone socket, will indicate the area of contact when viewed by the physician through the contact surface. Viewing the area of contact during the operation with the contact device in place is not always convenient and does not always yield the most efficient results for proper size determination.

As illustrated by the background art, efforts are continuously being made in an attempt to improve bone size gauging. No prior effort, however, provides the benefit attendant with the present invention. Additionally, the prior patents and commercial techniques do not suggest the present inventive combination of component elements arranged and configured as disclosed and claimed herein.

The present invention achieves its intended purposes, objects, and advantages through a new, useful and unobvious combination of component elements, with the use of a minimum number of functioning parts, at a reasonable cost to manufacture, and by employing only readily available materials.

Therefore, it is an object of this invention to provide an improved bone size testing method and apparatus comprising a hemispherical member having a pole on its axis at the distal end and having a bore on its axis at its proximal end; a handle releasably attached to the bore of the hemispherical member; and a pressure responsive surface on the hemispherical member for changing characteristics when brought in contact with a bone socket to be gauged.

It is a further object of the present invention to utilize the area of contact between a hemispherical test device and the bone socket receiving the ball joint in order to effect a readable variation on the surface of the device as effected by the contact.

It is a further object of this invention to change the characteristics, color or shape, of the exterior surface of a hemispherical gauge while in a bone socket sized and to interpret the changes as an indication of the fit between the socket and the gauge.

It is a further object of the present to sequentially insert a plurality of different sized hemispherical gauges into an essentially hemispherical socket in order to determine the best size fit of a ball for the socket.

The foregoing has outlined some of the more pertinent objects of this invention. These objects should be construed to be merely illustrative of some of the more prominent features and applications of the present invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with the specific embodiment shown in the attached drawings. For the purpose of summarizing the invention, the invention may be incorporated into an improved device for gauging the size of a bone socket comprising a hemispherical member having a pole on its axis at the distal end and having a bore on its axis at its proximal end; a handle releasably attached to the bore of the hemispherical member; and a pressure responsive surface on the hemispherical member for changing characteristics when brought in contact with a bone socket to be gauged.

The hemispherical member may be formed of a rigid, non-deformable material and the pressure responsive surface may be formed of a film adhered to the surface of the hemispherical member. The film changes color upon the application of pressure. The handle includes resilient means for indicating the proper pressure applied to the hemispherical member. The hemispherical member may be formed of a mass of deformable material. The surface of the mass of deformable material changes shape to conform to a bone socket to be gauged when brought in contact therewith. The device further includes a support structure within the mass of deformable material.

In addition, the invention may also be incorporated into an improved method for gauging the size of a bone socket to be provided with a hemispherical prosthetic device comprising providing a hemispherical member with a pressure responsive contact surface changeable in readable characteristic upon the application of pressure; inserting the contact surface into pressure contact with the bone socket to be sized; terminating the inserting and pressure contact of the contact surface when a predetermined pressure has been reached; withdrawing the contact surface; reading the contact surface which has been changed in characteristics.

The change in readable characteristic may be a change in color. The method further includes the repeating of the above steps if the majority of the contact surface has not been discolored as indicative of the determination of the proper size. The change in readable characteristics may be a change in shape of a deformable material.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the disclosed specific embodiment may be readily utilized as a basis for modifying or designing other methods or structures for carrying out the same purpose of the present invention. It should be realized by those skilled in the art that such equivalent methods and structures do not depart from the spirit and scope of the invention as set forth in the appended claims.

BRIEF DESCRIPTION OF THE DRAWINGS

For a fuller understanding of the nature and objects of the present invention, reference should be made to the following detailed description taken in conjunction with the accompanying drawings in which:

FIG. 1 is a perspective illustration of a bone testing gauge constructed in accordance with the principles of the primary embodiment of the present invention shown in association with a receptive bone socket.

FIG. 2 is also a perspective illustration of the gauge shown in FIG. 1 but viewed from the opposite side thereof.

FIG. 3 is an enlarged sectional view of the gauge shown in FIGS. 1 and 2 taken along the axis thereof.

FIG. 4 is an enlarged sectional view of the coupling between the handle end of the hemispherical member and the distal end of the handle.

FIG. 5 is a sectional view of a gauge constructed in accordance with an alternate embodiment of the invention.

Similar reference characters refer to similar parts throughout the several Figures.

DETAILED DESCRIPTION OF THE INVENTION

Shown in the Figures is a bone testing device or gauge 10 constructed in accordance with the principles of the present invention. The main component of the device is a hemispherical member 12. The member is constructed of an FDA approved medical grade material which is hard and which will not deform under normal pressures to which it is intended to be subjected. Typical of such material are NYLON and DELRAN. NYLON and DELRAN Trademarks of E. I. Du Pont de Nemours of Wilmington, Del.

Located at its axis on its end point is its forward or distal pole 14. From the pole at the forward or distal end, the device extends rearwardly or proximally and includes an equator plane 16 at an intermediate location. The plane 16 extends transverse to the medial line or axis. The gauge 10 is shown with a chamfered edge 18 extending radially inwardly and terminating in an axial bore 20. The axial bore is of sufficient size as to receive a cylindrical member 22. The cylindrical member has an interior surface 24 for receiving the end of the handle. Its exterior surface 26 is sized for being received tightly within the bore 20 by a press fit. A cannulation 28 is utilized to preclude mutual rotation. The exerior surface 26 is shown as circular, but to preclude inadvertent rotation within the hemispherical member, any convenient shape and size to preclude rotation could readily be utilized. The proximal end of the cylindrical member is flat for constituting a surface which may be placed on a flat table or the like with the hemispherical member extending upwardly for inspection.

A second part of the device is a rod which functions as a handle 30 for the surgeon using the device. The rod is actually a two-piece member, each member being elongated in length and cylindrical in cross-sectional configuration. One of the members 32, the proximal member, is provided with an enlarged cylindrical recess 34 at its distal end, the recess is of such size for receiving the proximal end of the distal member 36. The members are coupled together by a mutually cooperable flange 38 and collar 40. The flange and collar are such as to allow coupling and separation of members 32 and 36 upon the application of an axial force.

Interior of the recess 34 and between the two members 32 and 36 is a coil spring 44 positioned so that the proximal member 32 may be pushed distally with respect to the distal member 36 upon the application of force by a surgeon holding the proximal member 32. When the handle is held by the proximal member and moved distally, both members will move distally together. When, however, a force is encountered at the distal end of the distal member as by the contact surface contacting the socket S being sized, the force pushing the handle distally toward the socket S will compress the spring 44. Such compression will continue until the distal surface 46 of the proximal member has contacted the proximal edge of an abutment member 48 on the distal member. When such contact occurs, a predetermined force is being applied by the handle 30 as determined by the coefficient of restitution of the particulary selected spring. An operator, an orthopedic surgeon in the present invention, may thus grasp the device by the handle and insert the hemispherical member into the socket and apply pressure until the abutment surface 48 on the distal member 36 is contacted by the distal edge 46 of the proximal member 32. At this time, the surgeon will know that a predetermined pressure, for the particular application, has been reached and the contact surface 52 may be removed and viewed and read to indicate the size of the socket.

Coupling between the handle and the cylindrical member is through a quick release mechanism 56, shown in FIGS. 3 and 4 A U-shaped member 58 is formed with a short locking end 60 coupled through a central extent 62 to a long release button end 64. The U-shaped member 58 is located in a similarly configured U-shaped opening 66 in the distal portion of the handle. A spring 68 is located in a recess of the handle to urge the U-shaped member upwardly so that the short end 60 is secured in a complimentary recess 70 of the cylindrical member. In this condition, the longer button end is located exterior of the cylindrical member for being depressed by an operator to effect coupling and/or uncoupling of the handle with respect to the hemispherical member.

One additional component of the present invention is the pressure responsive layer 52 constituting the external contact surface of the hemispherical member. A wide variety of appropriate pressure responsive materials could be utilized on the surface of the hemispherical member. In the preferred embodiment, one particular type of pressure responsive material found suitable for the intended purpose is FUJI PRESCALE FILM as manufactured by Fuji Photo Film Company, Ltd. of Tokyo, Japan. Such film is a commercially available product. It includes a layer of microcapsule material on the interior surface of a polyethylene terpthalate (PET) base, the A film. A color developing layer is adhered to the other polyethylene terepthalate base, the C film. With the film layers in facing contact and with the microcapsule layer in contact with the color developing layer, a pressure of the magnitude generated between the exterior surfaces of the film will effect a discoloration in the region of the film where the pressure has occured turning the film of a first color, as for example white, to a second color which contrasts with respect to the first color, as for example blue, in those areas where pressure was applied. Such film is also available in single sheet type films and may be substituted as an alternative. The two sheet type film has been found to be preferred.

In order to apply an essentially uniform layer of film to the external surface of the hemispherical member, a strip of film is cut to a shape so as to fully cover the hemispherical member. Such piece is then coupled to the surface of the hemispherical member as by heat shrinking.

When the film is coupled to the surface of the hemispherically shaped member, an entire hemispherical contact surface is formed in conforming contact with the surface of the hemispherical member. In this manner, the entire surface, or essentially the entire surface, of the hemispherical member will constitute a contact surface for responding to pressure generated by contact with the socket bone to be sized. This allows for proper application of a properly sized artificial prosthetic device. The hemispherical member with its surface film and handle thus constitute a gauge.

The material for the film is sterile. Any other selected material for use for such function must, likewise, be sterile or sterilizable. Similarly, the hemispherical member as well as the handle must also be sterile or sterilizable. The handle is not disposable and may be sterilized on site as in an autoclave after each use. However, the hemispherical and cylindrical members are disposable and, after fabrication, they are gamma irradiated and packed, as in a blister pack, for retention of sterility and use.

Packing of the hemispherical and cylindrical members is preferably accomplished by first wrapping in a blister pack and then positioning in a rigid container such as a box. To accomplish proper packing, the cylindrical member is provided with an annular recess 74. Such recess is positionable in a mating aperture of one wall of the box. In this manner, the flat proximal face of the hemispherical member is located flush with one interior face of the apertured wall of the box. The other walls of the box are fixedly positioned with respect to the apertured wall so as to be positioned out of contact with the exterior surface of the hemispherical member. In this manner, the walls of the packing container will not improperly contact the exterior surface of the hemispherical member for changing the characteristics of the surface.

Removal of the hemispherical and cylindrical members from the box and blister pack is preferably accomplished by forming a hole in the blister pack over the end of the cylindrical member to expose the handle receiving bore 20 of the cylindrical member. The hole is covered by a peel-off top. The hemispherical member can then effectively be grasped by the operator by grasping the exposed exterior surface of the cylindrical member which extends outside the box. Upon removal of the peel-off top, the handle may then be inserted therein. The release button end 64 would be depressed radially inwardly to depress the locking end 60 inwardly so that the end of the handle may move into the cylindrical member. When the release button end 64 is released, the locking end 60 will move into the locking recess 70 for properly coupling the handle and the hemispherical member. The remainder of the packing, including the box and blister pack material can then be readily removed without any contact or pressure being applied against the exterior surface of the hemispherical member.

In carrying out the method of the present invention, the apparatus as described above is utilized as a gauge for socket bone size testing or gauging purposes. A plurality of such gauges as described above are first provided. Such plurality constitutes a set of similar gauges but fabricated of different sizes. It has been found that normal bone sockets are generally hemispherical and range in size from a diameter of 36 to 72 millimeters. As such, 37 gauges of sizes 36 to 72 millimeters in diameter in one millimeter increments would be provided. The attending surgeon would then estimate the size of the socket of the patient who is to be provided with an artificial bone, including a ball, for placement in the patient's socket. Such estimate is based on observing the patient's x-rays with templates and overlays. In an average size person, a 50 millimeter gauge would be provided along with a 49 and 51 millimeter gauge for use in the event that the socket was larger or smaller than initially estimated.

During the surgery, when the socket is exposed, the doctor would clean the socket and then insert the first gauge as, for example, a 49 millimeter gauge. If the gauge was too small and the socket too large, only the pole of the gauge would contact the socket. The surgeon would utilize the handle to press the gauge into place applying pressure until the coil spring had compressed and the distal edge of the proximal member contacted the abutment surface on the distal member. In such condition, the proper pressure of between about 5 and 20 lbs. would have been provided. Upon pulling out the gauge and observing it, only the tip or pole of the gauge would be discolored since the socket was large, the gauge was small and no, or minimum, side contact was made.

The physician would then repeat the process but with a larger gauge, as for example the 51 millimeter gauge. In such a condition, the socket would be too small, the gauge too large and only an equatorial, circumferential ring on the gauge would be contacted and discolored by the exterior peripheral edge of the bone. The pole would not be discolored since it did not contact the medial wall of the socket. Further, the proximal edge of the gauge would not be discolored due to lack of contact and pressure.

In the last test, the properly sized 50 millimeter gauge would be inserted and the majority of the gauge would be discolored by a smooth, constant contact, at the pole and over an extended circumferential ring, over the majority of its contact surface. The doctor or anyone else may read the contact surface and readily determine the size of the socket and the proper size of the ball to be inserted therein simply by observing the discoloration appearing on the contact surface.

In this manner, the gauge including the set of gauges of the present invention can be utilized to determine the size of a socket in a rapid and efficient manner without relying upon the expertise and experience of the attending surgeon in making such fit.

It is preferred that the material of the hemispherical member be opaque to allow for better visual contrast between the film, either colored or not colored, as compared with its backing surface which is the material of the hemispherical member.

FIG. 5 illustrates an alternate embodiment of the invention. According to that embodiment, the handle 80 is the same in structure and function as that of the primary embodiment, a spring loaded quick release mechanism. Its distal end 82, however, removably couples with a rigid, or essentially rigid, support frame or structure 84. The support structure has a central, elongated, cylindrical rod 86 removably coupled at its proximal end with the distal end of the handle. Between the distal end and proximal area of the rod, and secured thereto, are a plurality of flat, radially extending disks of varying diameter. The smallest disk 90 is adjacent to the distal end of the device. Such smallest disk 90 is of a mushroom shaped configuration. A further disk 92 is located adjacent to the proximal end of the apparatus. Between the smallest disk 90 and largest disk 92 are a plurality of additional disks 94 and 96. Such additional disks are of constantly increasing diameters when measured from the smallest disk 90 toward the largest disk 92. The exterior radial edges of the disks when taken together generally conform to the hemispherical shape of the hemispherical member.

The rod 86 and disks 90 through 96 support and provide rigidity to the central part of a mass 100 of deformable material. The deformable material is moldable and initially formed in a hemispherical shape and held upon the support structure 84. The exterior surface 102 of the deformable material 100 extends radially outwardly from the rod and disks to allow the exterior surface of the cylindrical member to deform when external pressure is applied thereto and to conform to a socket S when inserted therein. Under such circumstances, there will be little or no deformation of the internal extent of the material. The external extent of the material, however, will become reshaped, changing its shape charactertistics to correspond to the socket into which it is being inserted. During insertion for gauging, the excess surface material of the mass will move in a direction toward the handle so as not to interfere with removal of the gauge for subsequent observation and reading. To accommodate this deformation, the diameter of the ring 92 is less than the diameter of the hemispherically shaped material being deformed.

Upon removal of the gauge, after it has deformed to correspond to the size and shape of the socket, it is observed and read as by ring gauges of known sizes or by a caliper or the like. In this manner, an artificial bone may be precisely selected and utilized as a replacement.

The material for the hemispherical member of this alternate embodiment is any commercially available, bio-compatible material which deforms under pressure to conform to adjacent surfaces with which it makes pressure contact. Suitable materials include those used by dentists for making impressions of mouths as for sizing caps, crowns, bridges, false teeth, etc.

Specific materials which may be utilized in the second embodiment of the invention include ALGINATE IMPRESSION MATERIAL manufactured and sold by Dentply International, Inc. of Milford, Del. and Impergum F manufactured by Premier Dental Products Company of North Town, Pa.

The present disclosure includes that contained in the appended claims as well as that of the foregoing description. Although this invention has been described in it preferred forms with a certain degree of particularity, it is understood that the present disclosure of the preferred forms has been made only by way of example and numerous changes in the details of construction and combination and arrangement of parts may be resorted to without departing from the spirit and scope of the invention.

Now that the invention has been described, what is claimed is:

1. A device for gauging the size of a bone socket comprising:
   a hemispherical member having a pole on its axis at the distal end and having a bore on its axis at its proximal end;
   a handle releasably attached to the bore of the hemispherical member; and
   a pressure responsive surface means on the hemispherical member for changing characteristics when brought in contact with a bone socket to be gauged.

2. The device as set forth in claim 1 wherein the hemispherical member is formed of a rigid, non-deformable material and the pressure responsive surface is formed of a film coupled to the hemispherical member.

3. The device as set forth in claim 2 wherein the film changes color characteristics upon application of pressure.

4. The device as set forth in claim 1 wherein the handle includes resilient means for indicating a proper pressure applied to the hemispherical member.

5. The device as set forth in claim 1 wherein the hemispherical member is formed of a mass of deformable material.

6. The device as set forth in claim 5 wherein the surface of the mass of deformable material changes shape characteristics to conform to a bone socket to be gauged when brought in pressure contact therewith.

7. The device as set forth in claim 6 and further including a support structure within the mass of deformable material.

8. A method for gauging the size of a bone socket to be provided with a hemispherical prosthetic device comprising:

providing a hemispherical member with a pressure responsive contact surface changeable in readable characteristic upon the application of pressure;

inserting the contact surface into pressure contact with the bone socket to be sized in order to change the contact surface;

terminating the inserting and pressure contact of the contact surface when a predetermined pressure has been reached;

withdrawing the contact surface;

reading the contact surface which has been changed in characteristic.

9. The method as set forth in claim 8 wherein the change in readable characteristic is a change in color.

10. The method as set forth in claim 9 and further including the repeating of the above steps if the majority of the contact surface has not been discolored as indicative of the determination of the proper size.

11. The method as set forth in claim 8 wherein the change in readable characteristic is a change in shape of a deformable material.

* * * * *